United States Patent

Ohashi et al.

[11] Patent Number: 5,221,757
[45] Date of Patent: Jun. 22, 1993

[54] AMIDE DERIVATIVES AND DERMATOLOGIC PREPARATIONS CONTAINING THE SAME

[75] Inventors: Yukihiro Ohashi, Utsunomiya; Mituo Suda, Ichigai; Shinji Yano, Iwade; Akira Kawamata, Utsunomiya; Minehiro Okuda, Takatsuki; Genji Imokawa, Utsunomiya, all of Japan

[73] Assignee: Kao Corporation, Tokyo, Japan

[21] Appl. No.: 794,980

[22] Filed: Nov. 20, 1991

Related U.S. Application Data

[63] Continuation-in-part of Ser. No. 524,864, May 18, 1990, Pat. No. 5,175,321.

[30] Foreign Application Priority Data

May 19, 1989 [JP] Japan .................................. 1-126461
May 19, 1989 [JP] Japan .................................. 1-126462

[51] Int. Cl.⁵ .......................................... C07C 235/00
[52] U.S. Cl. ........................................ 554/66; 554/61
[58] Field of Search .......................... 554/63, 61, 66; 514/625, 873

[56] References Cited

FOREIGN PATENT DOCUMENTS 0227994 7/1987 European Pat. Off. .
216852 9/1988 Japan .

OTHER PUBLICATIONS

Chemical Abstracts 110:94523n.

Primary Examiner—José G. Dees
Assistant Examiner—Deborah D. Carr
Attorney, Agent, or Firm—Birch, Stewart, Kolasch & Birch

[57] ABSTRACT

An amide derivative represented by the following general formula (II):

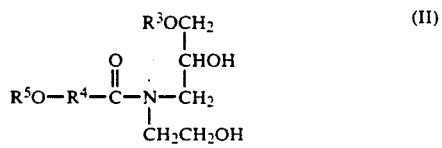

(wherein $R^3$ represents a straight-chain or branched, saturated or unsaturated hydrocarbon group carrying 10 to 40 carbon atoms; $R^4$ represents a straight-chain or branched hydrocarbon group carrying 3 to 39 carbon atoms; and $R^5$ represents a hydrogen atom, a straight-chain or branched, saturated or unsaturated hydrocarbon group carrying 10 to 40 carbon atoms or an acyl group); and a dermatologic preparation containing the same.

2 Claims, No Drawings

AMIDE DERIVATIVES AND DERMATOLOGIC PREPARATIONS CONTAINING THE SAME

This application is a continuation-in-part of application Ser. No. 07/524,864 filed on May 18, 1990, now U.S. Pat. No. 5,175,321.

BACKGROUND OF THE INVENTION

1. Field of the Invention

This invention relates to novel amide derivatives and dermatologic preparations containing the same. More particularly, it relates to dermatologic preparations capable of essentially improving the barrier functions of the horny layer, namely, maintaining normal barrier functions and restoring damaged barrier functions.

2. Description of the Prior Art

The horny layer is located on the outermost side of the skin to cover the whole body to thereby protect the body from external irritation and invasion of foreign substances and inhibit the evaporation of the moisture contained in the body.

When these barrier functions of the horny layer are weakened by some reasons, the skin frequently suffers from troubles such as inflammation or chapping.

Furthermore, it is known that poverty or deficiency of essential fatty acids (for example, arachidonic acid or linoleic acid), which is caused by prolonged intake of foods free from essential fatty acids, would be accompanied by disorders in the barrier functions of the horny layer.

As the results of analyses on intercellular lipids, it has been found out that the intercellular lipids of the horny layer, in particular, O-acylceramide significantly contributes to the maintenance of the above-mentioned barrier functions of the horny layer.

It is believed, furthermore, that lipids secreted from sebaceous glands form a sebaceous membrane on the surface of the skin so as to partially make up for the barrier functions of the horny layer. Thus dermatologic preparations containing, for example, vaseline have been used in order to form a coating on the surface of the skin so as to make up for the barrier functions of the horny layer.

However known dermatologic preparations cannot essentially improve the barrier functions of the horny layer but merely form a tentative coating on the surface of the skin so as to make up for the barrier functions.

SUMMARY OF THE INVENTION

It is an object of the present invention to provide dermatologic preparations capable of maintaining the normal barrier functions of the horny layer and restoring damaged barrier functions. Namely, the dermatologic preparation of the present invention can essentially improve the barrier functions of the horny layer so as to suppress inflammation and chapping.

In order to achieve the above-mentioned object, the present inventors have conducted extensive studies. As a result, they have found out that dermatologic preparations containing novel amide derivatives represented by the following general formula (I) or (II) can essentially improve the barrier functions of the horny layer, thus completing the present invention:

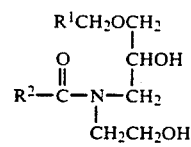

(wherein $R_1$ and $R_2$ represent each a straight-chain or branched, saturated or unsaturated hydrocarbon group provided that one of them carries 26 to 39 carbon atoms while the other carries 9 to 39 carbon atoms);

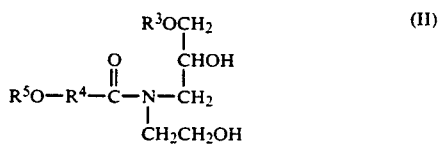

(wherein $R^3$ represents a straight-chain or branched, saturated or unsaturated hydrocarbon group carrying 10 to 40 carbon atoms; $R^4$ represents a straight-chain or branched hydrocarbon group carrying 3 to 39 carbon atoms; and $R^5$ represents a hydrogen atom, a straight-chain or branched, saturated or unsaturated hydrocarbon group carrying 10 to 40 carbon atoms or an acyl group).

Accordingly, the present invention provides a novel amide derivative represented by the above general formula (I), a novel amide derivative represented by the above general formula (II) and dermatologic preparations containing at least one of these amide derivatives.

The dermatologic preparations of the present invention containing the amide derivatives of the present invention represented by the above general formula (I) or (II) are effective in essentially improving the barrier functions of the horny layer. When applied to the skin, they can suppress inflammation and chapping.

DETAILED DESCRIPTION OF THE INVENTION

First, the amide derivative of the present invention represented by the above-mentioned general formula (I) will be described.

The amide derivative of the present invention represented by the above-mentioned general formula (I) may be prepared in accordance with a known method described in, for example, Japanese Patent Laid-Open No. 216852/1988. That is, it may be obtained according to the following reaction scheme wherein a compound (III) prepared from glycidyl ether and ethanolamine is reacted with a fatty acid lower alkyl ester in the presence of a base catalyst while distilling off the lower alcohol thus formed:

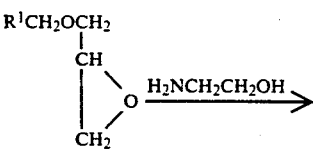

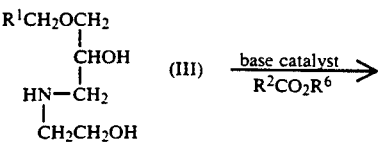

-continued

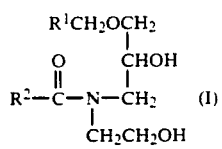

(wherein $R^1$ and $R^2$ are as defined above; and $R^6$ represents an alkyl group carrying one to five carbon atoms).

Next, the amide derivative of the present invention represented by the above-mentioned general formula (II) will be described.

The method for preparing the amide derivative of the present invention represented by the general formula (II) is not particularly restricted. Thus it may be prepared by, for example, the following methods (1) to (3).

(1) Method for preparing an amide derivative (II-A) of the general formula (II) wherein $R^5$ is a hydrogen atom:

This derivative (II-A) may be prepared in accordance with a known method described in, for example, Japanese Patent Laid-Open No. 216852/1988. According to the following reaction scheme, an amine derivative (IV) prepared from glycidyl ether and ethanolamine is reacted with a hydroxy fatty acid lower alkyl ester (V-A) or a hydroxy fatty acid lactone (VI) in the presence of a base catalyst while distilling off the lower alcohol thus formed:

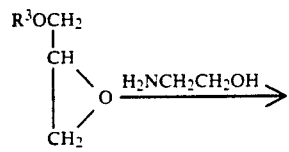

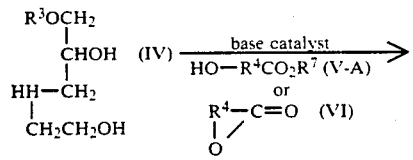

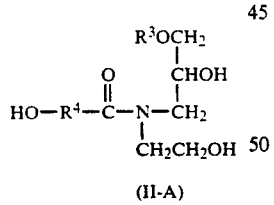

(II-A)

(wherein $R^3$ and $R^4$ are as defined above; and $R^7$ represents an alkyl group carrying one to five carbon atoms).

(2) Method for preparing an amide derivative (II-B) of the general formula (II) wherein $R^5$ is a straight-chain or branched, saturated or unsaturated hydrocarbon group carrying 10 to 40 carbon atoms:

This derivative (II-B) may be prepared in accordance with the following reaction scheme wherein a hydroxy fatty acid (V) or a hydroxy fatty acid ester (V-A) is reacted with an alkyl halide (VII) or an alkyl sulfonate (VIII) in the presence of a base to give an etherified fatty acid ester (V-B), which is then reacted with an amide derivative (IV) obtained by the above method (1) in the presence of a base catalyst while distilling off the alcohol thus formed:

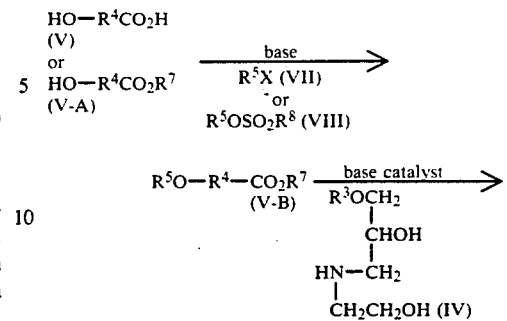

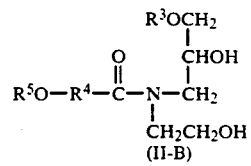

(II-B)

(wherein $R^3$, $R^4$ and $R^7$ are as defined above; $R^5$ represents a straight-chain or branched, saturated or unsaturated hydrocarbon group carrying 10 to 40 carbon atoms; $R^8$ represents a methyl, phenyl or p-tolyl group; and X represents a chlorine, bromine or iodine atom).

(3) Method for preparing an amide derivative (II-C) of the general formula (II) wherein $R^5$ is a straight-chain or branched, saturated or unsaturated acyl group carrying 10 to 40 carbon atoms:

This derivative (II-C) may be prepared according to the following reaction scheme wherein a hydroxy fatty acid ester (V-A) is condensed with a fatty acid (IX) in the presence of an appropriate dehydrating agent [such as

and $P(C_6H_5)_5$] to given an acylated fatty acid ester (V-C), which is then reacted with the amide derivative (IV) obtained by the above method (1) in the presence of a base catalyst while distilling off the alcohol thus formed:

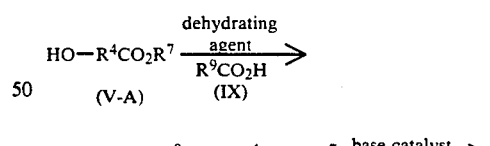

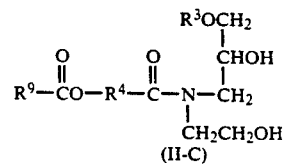

(II-C)

(wherein $R^3$, $R^4$ and $R^7$ are as defined above; and $R^9$ represents a straight-chain or branched, saturated or unsaturated hydrocarbon group carrying 9 to 39 carbon atoms).

Alternately, the above-mentioned amide derivative (II-C) may be prepared in accordance with the following reaction scheme with the use of an appropriate protective group.

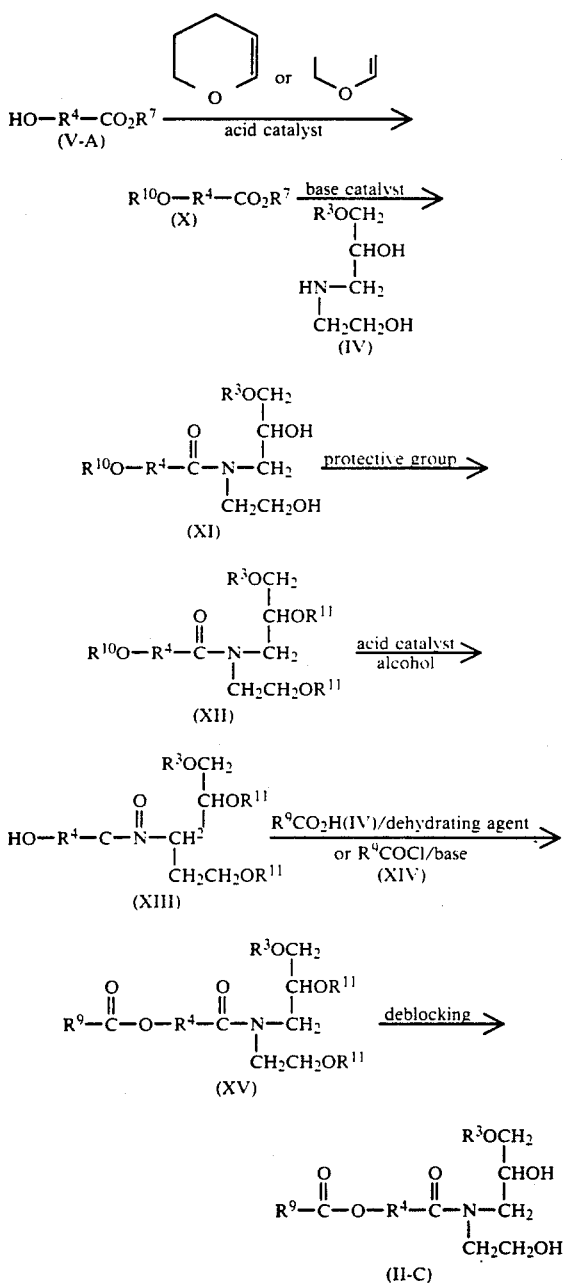

(wherein $R^3$, $R^4$, $R^7$ and $R^9$ are as defined above; $R^{10}$ represents a

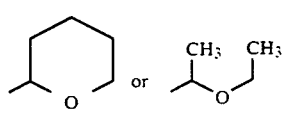

group; and $R^{11}$ represents an acetyl or tert-butyldiphenylsilyl group).

Namely, the hydroxy group of a hydroxy fatty acid ester (V-A) is blocked with an etheric protective group $R^{10}$ such as a tetrahydropyranyl or ethoxyethyl group and then reacted with an amine derivative (IV) in the presence of a base catalyst to thereby give an amide derivative (XI). After blocking the two hydroxy groups of the amide derivative (XI) with acetyl or tert-butyldiphenylsilyl groups ($R^{11}$), the compound is treated with an alcohol in the presence of an acid catalyst to thereby eliminate the protective group $R^{10}$ (deblocking). The amide derivative (XIII) thus obtained is then treated with a fatty acid (IX) in the presence of an appropriate dehydrating agent [for example, $$\underset{EtOC-N=N-COEt}{\overset{O\quad\quad O}{\|\quad\quad\|}}$$

and $P(C_6H_5)_3$]. Alternately, it is treated with a fatty acid chloride (XIV) in the presence of a base. Thus an amide derivative (XV) is obtained. Finally, the protective group $R^{11}$ is eliminated by using a base such as $K_2CO_3$ or $Na_2CO_3$ in a lower alcohol (when $R^{11}$ is an acetyl group) or by using a fluoride ion of, for example, tetrabutylammonium fluoride (when $R^{11}$ is a tertbutyldiphenylsilyl group) to thereby give an amide derivative (II-C).

Next, the dermatologic preparation of the present invention containing the amide derivative (I) or (II) of the present invention represented by the above general formula (I) or (II) will be described.

The content of the amide derivative (I) or (II) of the present invention in the dermatologic preparation of the present invention is not particularly restricted. In the case of an emulsion type preparation, the amide derivative (I) or (II) may be preferably contained in an amount of 0.001 to 50% (by weight, the same will apply hereinafter) based on the whole preparation. In the case of an oily preparation containing a liquid hydrocarbon such as squalane as a base, the amide derivative (I) or (II) may be preferably contained in an amount of 0.01 to 50%.

The dermatologic preparations of the present invention may be prepared by blending a base commonly used for dermatologic preparations with the amide derivative (I) or (II) of the present invention. The dermatologic preparations may be broadly classified into medicinal dermatologic preparations and cosmetics depending on the applications thereof.

Examples of the medicinal dermatologic preparations include various ointments containing medicinal ingredients. These ointments may contain either an oily base or an O/W or W/O emulsion base. The oily base is not particularly restricted and examples thereof include vegetable oils, animal oils, synthetic oils, fatty acids and natural and synthetic glycerides. The medicinal ingredients are not particularly restricted and, for example, analgesics, antiinflammatory agents, antipruritic agents, bactericides, astringents, skin emollients and hormones may be used therefor, if required.

In using the dermatologic preparations of the present invention as the cosmetic, the essential ingredient, i.e., the amide derivative (I) or (II) of the present invention may be arbitrarily blended with, for example, oleaginous components, humectants, ultraviolet absorbers, alcohols, chelating agents, pH modifiers, preservatives, thickeners, colorants and perfumes commonly employed in the art.

The dermatologic preparations may be formulated into various skin cosmetics including W/O and O/W emulsions, cream, cosmetic milky lotion, cosmetic lotion, lipstick, foundation, skin cleanser, hair tonic, hair styling lotion, hair nourishment and hair growth stimulant.

FUNCTION

The function mechanism of the dermatologic preparations of the present invention containing the amide derivative (I) or (II) of the present invention represented by the above-mentioned general formula (I) or (II) has not been completely clarified in detail. It is assumed, however, that the application thereof to the skin as the dermatologic preparation might serve to reinforce the intercellular lipid membrane of the horny layer so as to improve the barrier function of the horny layer.

To further illustrate the present invention, the following Examples will be given.

EXAMPLE 1

Synthesis of N-(2-hydroxy-3-hexadecyloxypropyl)-N-2-hydroxyethyltriacontanamide (Ia) [amide derivative of the general formula (I) wherein $R^1$ is $C_{15}H_{31}$ and $R^2$ is $C_{29}H_{59}$]

(1) Synthesis of N-(2-hydroxy-3-hexadecyloxypropyl)ethanolamine (IIIa)

61.1 g (1.0 mol) of ethanolamine was introduced into a 200-ml four-necked flask equipped with a stirrer, a dropping funnel, a thermometer and a reflux condenser and heated to 60° to 70° C. under stirring. 24.3 g (0.082 mol) of hexadecyl glycidyl ether was added dropwise thereto over a period of 45 minutes. After the addition was completed, the resulting mixture was heated and stirred under the same conditions as those described above for additional two hours. Then unreacted ethanolamine was distilled off under reduced pressure (79 to 81° C./20 Torr). The residue was purified by silica gel flash column chromatography to thereby give 18.4 g of the compound (IIIa) at a yield of 63%. The data of the $^1$H-NMR of the obtained compound are as follows:

$^1$H-NMR (δ, CDCl$_3$): 0.85 (t, 3H), 1.23 (bs, 28H), 2.6~2.8 (m, 4H), 3.1~3.9 (m, 10H).

(2) Synthesis of the Amide Derivative (Ia)

5.39 g (15 mmol) of the compound (IIIa) obtained in the above item (1) and 0.042 g (0.75 mmol) of KOH were introduced into a 50-ml flask equipped with a stirrer, a dropping funnel, a thermometer and a distilling tube. While stirring the mixture by heating under reduced pressure (90° C./20 Torr), 7.00 g (15 mmol) of methyl triacontanoate was added dropwise thereto over a period of 1.5 hours. After the completion of the addition, the mixture was further stirred under the same conditions as those described above for additional two hours. The crude product thus obtained was purified by silica gel flash column chromatography to thereby give 8.95 g the compound (Ia) at a yield of 75%. The melting point and IR and $^1$H-NMR data of the obtained compound are as follows:

m.p.: 82.2°~83.0° C.

IR: 3310, 2920, 2854, 1617, 1470, 1110, 1062, 720 cm$^{-1}$.

$^1$H-NMR (δ, CDCl$_3$): 0.88 (t, J=6.5 Hz, 6H), 1.01~1.73 (M, 82H), 2.31~2.45 (m, 2H), 3.08~4.28 (m, 13H).

EXAMPLE 2

Synthesis of N-(2-hydroxy-3-dotriacontyloxypropyl)-N-2-hydroxyethyltriacontanamide (Ib) [amide derivative of the general formula (I) wherein $R^1$ is $C_{31}H_{63}$ and $R^2$ is $C_{29}H_{59}$]

The procedure of Example 1 (1) was repeated except that the hexadecyl glycidyl ether was replaced with dotriacontyl glycidyl ether to thereby give the compound (Ib) in the form of a colorless powder at a yield of 71%. The melting point and IR and $^1$H-NMR data of the obtained compound are as follows:

m.p.: 88.2°~88.9° C.

IR: 3316, 2920, 2854, 1617, 1467, 1107, 1059, 720 cm$^{-1}$.

$^1$H-NMR (δ, CDCl$_3$): 0.88 (t, J=6.6 Hz, 6H), 0.99~1.72 (m, 114H), 2.25~2.45 (m, 2H), 2.95~4.28 (m, 13H).

EXAMPLE 3

Synthesis of N-(2-hydroxy-3-dotriacontyloxypropyl)-N-2-hydroxyethylhexadecanamide (Ic) [amide derivative of the general formula (I) wherein $R^1$ is $C_{31}H_{63}$ and $R^2$ is $C_{15}H_{31}$]

The procedure of Example 1 was repeated except that the hexadecyl glycidyl ether used in Example 1 (1) was replaced with dotriacontyl glycidyl ether and the methyl triacontanoate used in Example 1 (2) was replaced with methyl hexadecanoate to thereby give the compound (Ic) in the form of a colorless powder at a yield of 80%. The melting point and IR and $^1$H-NMR data of the obtained product are as follows:

m.p.: 62.6°~64.0° C.

IR: 3304, 2920, 2854, 1617, 1467, 1056, 720 cm$^{-1}$.

$^1$-NMR (δ, CDCl$_3$): 0.88 (t, J=6.6 Hz, 6H), 0.98~1.71 (m, 86H), 2.25~2.48 (m, 2H), 3.24~4.25 (m, 13H).

EXAMPLE 4

The dermatologic preparations of the present invention comprising 10% of each of the amide derivatives of the present invention listed in Table 1 and 90% of squalane were prepared. Then the transepidermal water loss and percutaneous absorption of each dermatologic preparation were evaluated in the following manner. For comparison, a comparative dermatologic preparation comprising squalane alone was also evaluated. Table 1 summarizes the results.

Test Method

Wistar male rats were fed with a feed free from essential fatty acids. Then each dermatologic preparation was applied to the shaven dorsal skin of the rat showing essential amino acid deficiency once a day for three weeks. On the next day of the completion of the application for three weeks, the following items were examined.

Each lot involved three rats.

(1) Transepidermal Water Loss

The dorsal skin of the rat was washed with water at 37° C. and the animal was allowed to stand in a room at 20° C. under a humidity of 45% for an hour. Then the transepidermal water loss was measured with an evaporimeter. A larger water loss means lower barrier functions of the horny layer and more serious chapping.

When the normal barrier functions are maintained, this value is smaller than 10. On the other hand, an essential fatty acid deficient rat having damaged barrier functions shows a value exceeding 35. Each value is expressed in "mean ± standard deviation".

(2) Percutaneous Absorption

The dorsal skin of the rat was washed with water at 37° C. Next, said skin was cut and inserted into a percutaneous absorption chamber with the epidermal side thereof directed upward. A lower receiver of the chamber was filled with a phosphate buffer equilibrated salt solution while a container on the epidermal side thereof was charged with 1 ml of a solvent containing 37 KBq of $^{14}$-C-salicyclic acid. After two hours, the amount of the $^{14}$C-salicylic acid penetrating into the lower receiver was determined. When the normal barrier functions are maintained, the $^{14}$C-salicylic acid scarcely penetrates after two hours. This value increases as the barrier functions are more seriously damaged. Each value is expressed in "mean ± standard deviation".

TABLE 1

| Amide derivative | Transepidermal water loss | Percutaneous absorption |
| --- | --- | --- |
| Product of Invention | | |
| compound of Ex. 1 (Ia) | 29.2 ± 6.8 | 546 ± 260 |
| compound of Ex. 2 (Ib) | 20.8 ± 7.2 | 778 ± 265 |
| compound of Ex. 3 (Ic) | 18.6 ± 4.8 | 546 ± 320 |
| Comparison | | |
| squalane alone | 35.8 ± 9.6 | 1220 ± 240 |

EXAMPLE 5

By using each of the amide derivatives of the present invention, the dermatologic preparations of the present invention of the compositions as specified in Table 2 (emulsion cosmetic) were prepared. The effect of each product of improving skin chapping was evaluated in the following manner. For comparison, a dermatologic preparation free from any amide derivative of the present invention (comparative product) was evaluated in the same manner. Table 3 summarizes the results.

Test Method

Ten female subjects aged 20 to 40 years, who suffered from chapping in cheeks in winter, were employed. Different dermatologic preparations were applied on the right and left cheeks of the subjects once a day for three weeks. On the next day of the completion of the application for three weeks, the following items were examined.

(1) Transepidermal Water Loss

The face of each subject was washed with water at 37° C. and then she was allowed to stand in a room at 20° C. under a humidity of 45% for an hour. Then the transepidermal water loss was measured with an evaporimeter. A larger water loss means lower barrier functions of the horny layer and more serious chapping. When this value exceeds 40, serious chapping is observed. When it is smaller than 10, on the other hand, scarcely any chapping is observed. Each value is expressed in "mean ± standard deviation".

(2) Skin Chapping Score

Skin chapping was observed with the naked eye and evaluated based on the following criteria. Each score is expressed in "mean ± standard deviation".

| score | Evaluation of chapping |
| --- | --- |
| 0 | no chapping observed. |
| 1 | slight chapping observed. |
| 2 | chapping observed. |
| 3 | somewhat serious chapping observed. |
| 4 | serious chapping observed. |

TABLE 2

| | Invention products | (% by weight) Comparative product |
| --- | --- | --- |
| methyl-branched isostearyl glyceryl ether | 2.0 | 2.0 |
| 2-octyldodecyl myristate | 10.0 | 10.0 |
| vaseline | 3.0 | 3.0 |
| squalane | 5.0 | 5.0 |
| tocopherol acetate | 0.5 | 0.5 |
| amide derivative (refer to Table 3) | 1.0 | — |
| water | the balance | the balance |

TABLE 3

| Amide derivative | Transepidermal water loss | Skin chapping score |
| --- | --- | --- |
| Invention product | | |
| compound of Ex. 1 (Ia) | 24.3 ± 5.3 | 1.5 ± 0.3 |
| compound of Ex. 2 (Ib) | 19.8 ± 6.4 | 1.3 ± 0.4 |
| compound of Ex. 3 (Ic) | 17.6 ± 4.8 | 0.9 ± 0.3 |
| Comparative product | | |
| — | 28.6 ± 9.8 | 2.4 ± 0.7 |

EXAMPLE 6

Synthesis of N-(2-hydroxy-3-hexadecyloxypropyl)-N-2-hydroxyethyl-12-hydroxyoctadecanamide (II-Aa) [amide derivative of the general formula (II) wherein $R^3$ is $C_{16}H_{33}$ and $R^5O$—$R^4$ is

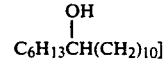

]

(1) Synthesis of N-(2-hydroxy-3-hexadecyloxypropyl)ethanolamine (IVa)

61.1 g (1.0 mol) of ethanolamine was introduced into a 200-ml four-necked flask equipped with a stirrer, a dropping funnel, a thermometer and a reflux condenser and heated to 60° to 70° C. under stirring. 24.3 g (0.082 mol) of hexadecyl glycidyl ether was added dropwise thereto over a period of 45 minutes. After the completion of the addition, the resulting mixture was stirred by heating under the same conditions as those described above for additional two hours. Then unreacted ethanolamine was distilled off under reduced pressure (79° to 81° C./20 Torr). The residue was purified by silica gel flash column chromatography to thereby give 18.4 g of the compound (IVa) at a yield of 63%. The $^1$H-NMR data of the obtained compound are as follows:

$^1$H-NMR (δ, CDCl$_3$): 0.85 (t, 3H), 1.23 (bs, 28H), 2.6~2.8 (m, 4H), 3.1~3.9 (m, 10H).

(2) Synthesis of Amide Derivative (II-Aa)

17 3 g (48 mmol) of the compound (IVa) obtained in the above item (1) and 0.14 g (2.5 mmol) of KOH were introduced into a 100-ml flask equipped with a stirrer, a dropping funnel, a thermometer and a distilling tube. While stirring the mixture by heating under reduced pressure (80° C./20 Torr), 15.1 g (48 mmol) of methyl 12-hydroxyoctadecanoate was added dropwise thereto over a period of an hour. After the completion of the addition, the mixture was further stirred under the same conditions as those described above for additional one hour. The crude product thus obtained was purified by silica gel flash column chromatography to thereby give 23.0 g the compound (II-Aa) at a yield of 74%. The melting point and IR and $^1$H-NMR data of the obtained compound are as follows:

m.p.: 70.8°~71.3° C.

IR: 3352, 2926, 2854, 1617, 1473, 1122, 1077 cm$^{-1}$.

$^1$H-NMR (δ, CDCl$_3$): 0.88 (t, J=6.3 Hz, 6H), 1.12~1.82 (m, 2H), 3.23~4.30 (m, 15H).

EXAMPLE 7

Synthesis of N-(2-hydroxy-3-hexadecyloxypropyl)-N-2-hydroxyethyl-16-hydroxyhexadecanamide (II-Ab) [amide derivative of the general formula (II) wherein R$^3$ is C$_{16}$H$_{33}$ and R$^5$OR$^4$ is HO(CH$_2$)$_{15}$]

The amine (IVa) obtained in Example 1 (1) was reacted with methyl 16-hydroxyhexadecanoate in the same manner as the one described in Example 1 (2) to thereby give the compound in the form of a colorless powder at a yield of 75%. The melting point and IR and $^1$H-NMR data of the obtained product are as follows:

m.p.: 80.6°~81.5° C.

IR: 3370, 2920, 2854, 1626, 1596, 1473, 1131, 1062, 723 cm$^{-1}$.

$^1$H-NMR (δ, CDCl$_3$): 0.88 (t, J=6.6 Hz, 3H), 0.96~1.80 (m, 54H), 2.30~2.48 (m, 2H), 3.24~4.17 (m, 15H).

EXAMPLE 8

Synthesis of N-(2-hydroxy-3-hexadecyloxyproxyl)-N-2-hydroxyethyl-16-(9Z,12Z-octadecadienyloxy)hexadecanamide (II-Ba) [amide derivative of the general formula (II) wherein R$^3$ is C$_{16}$H$_{33}$ and R$^5$O—R$^4$ is

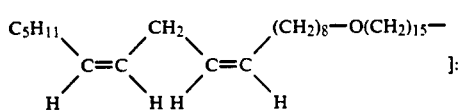
]:

(1) Synthesis of methyl 16-(9Z,12Z-octadecadienyloxy)hexadecanoate (V-Ba)

2.72 g (10 mmol) of 16-hydroxyhexadecanoic acid, 50 ml of dry tetrahydrofuran, 5 ml of dry hexamethylphosphoric triamide and 0.24 g (10 mmol) of sodium hydride were introduced into a 300-ml four-necked flask equipped with a stirrer, a dropping funnel, a thermometer and a reflux condenser and stirred at room temperature under a nitrogen gas stream for 30 minutes. Next, the mixture was cooled to −70° C. and 6.25 ml (10 mmol) of a 1.6N solution of butyllithium in hexane was added thereto. The resulting mixture was heated to room temperature over a period of 30 minutes and 0.24 g (10 mmol) of sodium hydride was added thereto. The mixture was further stirred at room temperature for additional 30 minutes. Then 9.25 g (22 mmol) of 9Z,12Z-octadecadienyl p-toluenesulfonate was added dropwise thereto and the mixture was heated to 65° C. under stirring for 18 hours. Then 150 ml of dry methanol was added to the reaction mixture and the resulting mixture was further stirred at 65° C. for an hour. The reaction mixture was cooled to room temperature and the excess alkali was neutralized with an aqueous solution of ammonium chloride. The reaction mixture was extracted with toluene and the solvent was distilled off under reduced pressure. Then the residue was purified by silica gel flash column chromatography to thereby give 0.72 g of the compound (V-Ba) at a yield of 13.5%.

(2) Synthesis of Amide Derivative (II-Ba)

The compound (V-Ba) obtained in the above item (1) was reacted with the amine (IVa) obtained in Example 1 (1) in the same manner as the one described in Example 1 (2). Thus the compound (II-Ba) was obtained in the form of a colorless powder at a yield of 71%. The melting point and IR and $^1$H-NMR data of the obtained compound are as follows:

m.p.: 63.0°~64.3° C.

IR: 3304, 2920, 2854, 1614, 1467, 1116, 1062, 720 cm$^{31}$ $^1$.

$^1$H-NMR (δ, CDCl$_3$): 0.80~0.95 (m, 6H), 0.95~1.70 (m, 72H), 1.95~2.12 (m, 4H), 2.39 (t, J=7.7 Hz, 2H), 2.77 (bt, J=5.8 Hz, 2H), 3.39 (t, J=6.6 Hz, 4H), 3.23~4.23 (m, 13H), 5.24~5.44 (m, 4H).

EXAMPLE 9

Synthesis of N-(2-hydroxy-3-hexadecyloxypropyl)-N-2-hydroxyethyl-16-(9Z,12Z-octadecadienoyloxy)hexadecanamide (II-Ca) [amide derivative of the general formula wherein R$^3$ is C$_{16}$H$_{33}$ and R$^5$O—R$^4$ is

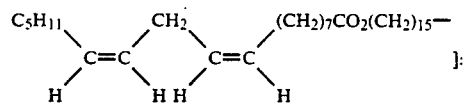
]:

(1) Synthesis of Methyl 16-(9Z,12Z-octadecadienoyloxy)hexadecanoate (V-Ca)

4.30 g (15 mmol) of methyl 16-hydroxyhexadecanoate, 8.41 g (13 mmol) of linoleic acid, 7.87 g (30 mmol) of triphenylphosphine and 100 ml of tetrahydrofuran were fed into a 300-ml flask equipped with a stirrer, a dropping funnel and a thermometer and 5.22 g (30 mmol) of diethyl azodicarboxylate was added dropwise thereto at room temperature under stirring over a period of an hour. After the completion of the addition, the mixture was further stirred at room temperature for four hours. After distilling off the solvent under reduced pressure, the residue was purified by silica gel flash column chromatography to thereby give 6.76 g of the compound (V-Ca) at a yield of 82%.

(2) Synthesis of Amide Derivative (II-Ca)

2.74 g (5 mmol) of the compound (V-Ca) obtained in the above item (1), 1.80 g (5 mmol) of the amine (IVa) obtained in Example 1 (1) and 0.028 g (0.25 mmol) of potassium tert-butoxide were fed into a 50-ml flask equipped with a stirrer, a dropping funnel, a thermometer and a distilling tube. Then the mixture was stirred by heating under reduced pressure (80° C./20 Torr) for 30 minutes. The crude product thus obtained was purified by silica gel column chromatography and gel chromatography to thereby give 1.65 g of the compound (II-Ca) at a yield of 38%. The melting point and IR, $^1$H-NMR and MS data of the obtained compound are as follows:

m.p.: 58.2°~58.9° C.

IR: 3304, 2920, 2856, 1734, 1612, 1464, 1440, 1216, 1166, 1108, 756, 720 cm$^{-1}$.

$^1$H-NMR ($\delta$, CDCl$_3$): 0.80~1.00 (m, 6H), 1.00~1.73 (m, 60H), 1.95~2.16 (m, 4H), 2.28 (t, J=7.5 Hz, 2H), 2.39 (bt, J=7.7 Hz, 2H), 2.77 (bt, J=5.9 Hz, 2H), 3.23~4.25 (m, 13H), 4.05 (t, J=6.6 Hz, 2H), 5.26~5.47 (m, 4H).

MS (FAB, POS): 877 (M+1), 859, 634, 596, 360. (FAB, NEG): 875 (M−1), 873, 831, 613, 534, 359, 305, 279.

EXAMPLE 10

L- Synthesis of N-(2-hydroxy-3-hexadecyloxypropyl)-N-2-hydroxyethyl-16-(9Z-octadecenoyloxy)hexadecanamide (II-Cb) [amide derivative of the above-mentioned general formula (II) wherein R$^3$ is C$_{16}$H$_{33}$— and

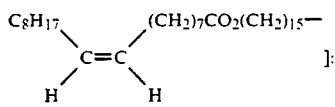

]:

(1) Synthesis of N-(2-hydroxy-3-hexadecyloxypropyl)-N-2-hydroxyethyl-16-(2-tetrahydropyranyloxy)hexadecanamide (XI-b)

100.26 g (0.35 mol) of methyl 16-hydroxyhexadecanoate, 0.60 g (3.5 mmol) of p-toluenesulfonic acid and 350 ml of dichloromethane were introduced into a 1-l flask equipped with a stirrer and a dropping funnel. 32.39 g (0.385 mol) of dihydropyran was added dropwise thereto while stirring at 0° C. After the completion of the addition, the mixture was stirred at room temperature for an hour to thereby complete the reaction. Next, the reaction mixture was neutralized by adding 0.59 g (7 mmol) of NaHCO$_3$. After filtering and removing solvent under reduced pressure; a crude product of methyl 16-(2-tetrahydropyranyloxy)hexadecanoate was obtained.

Next, 125.9 g (0.35 mol) of the N-(2-hydroxy-3-hexadecyloxypropyl)ethanolamine (IVa) obtained in the step (1) of Example 6 and 0.98 g (17.5 mmol) of KOH were introduced into a 1-l flask equipped with a stirrer, a dropping funnel, a thermometer and a distillation apparatus. Then the crude methyl 16-(2-tetrahydropyranyloxy)hexadecanoate obtained above was added dropwise thereto in 2 hours under stirring and heating to 80° C. under a reduced pressure of 20 Torr, while removing the methanol thus formed under reduced pressure. After the completion of the addition, the reaction mixture was stirred for additional 2 hours under the same conditions as those specified above. The obtained crude product was recrystallized from methanol to thereby give 212.3 g of the compound (XI-b) (yield: 86.9 %). (2) Synthesis of N- 2-(tert-butyldiphenylsilyloxy)-3-hexadecyloxypropyl -N-2-(tert-butyldiphenylsilyloxy)ethyl-16-hydroxyhexadecanamide (XIII-b):

34.91 g (0.05 mol) of the compound (XI-b) obtained in the above step (1), 13.62 g (0.2 mol) of imidazole and 350 ml of dimethylformamide were introduced into a 1-l flask equipped with a stirrer and a dropping funnel. 30.24 g (0.11 mol) of tertbutyldiphenylchlorosilane was added dropwise thereto while stirring at room temperature. Then the obtained mixture was heated to 50° C. and stirred for 14 hours. After the completion of the reaction, the reaction mixture was extracted with diethyl ether and washed with brine. Next, the solvent was removed under reduced pressure.

Then the residue obtained above was introduced into a 1-l flask equipped with a stirrer and 550 ml of ethanol, 150 ml of methanol and 2.36 g (9.4 mmol) of pyridinium p-toluenesulfonate were added thereto. The obtained mixture was then stirred at room temperature for 28 hours. After the completion of the reaction, the reaction mixture was neutralized with NaHCO$_3$ and extracted with diethyl ether. After removing the solvent under reduced pressure, the residue was purified by silica gel flash column chromatography. Thus 39.5 g of the compound (XIII-b) was obtained (yield: 72.4 %).

(3) Synthesis of Amide Derivative (II-Cb)

4.25 g (3.9 mmol) of the compound (XIII-b) obtained in the above step (2), 1.23 g (15.6 mmol) of pyridine and 50 ml of dichloromethane were introduced into a 200-ml flask equipped with a stirrer and a dropping funnel. 1.41 g of oleoyl chloride was added dropwise thereto under stirring at room temperature. After the completion of the addition, the mixture was stirred for additional one hour at room temperature to thereby complete the reaction. Then the reaction mixture was washed with water and the solvent was removed under reduced pressure. After removing highly polar by-products by silica gel short column chromatography, a crude product was obtained.

Then the crude product thus obtained was introduced into a 200-ml flask equipped with a stirrer. Further, 50 ml of tetrahydrofuran and 2.46 g (7.8 mmol) of tetrabutylammonium fluoride were added thereto and the obtained mixture was stirred at room temperature for 30 minutes. After the completion of the reaction, the reaction mixture was extracted with chloroform and washed with water. Then the solvent was removed under reduced pressure and the residue was purified by silica gel flash column chromatography. Thus 2.67 g of the title compound (II-Cb) was obtained (yield: 77.9 %). The melting point and IR and $^1$H-NMR data of the obtained compound are as follows:

m.p.: 60.4°~61.3° C.

IR: 3304, 2920, 2854, 1737, 1617, 1467, 1443, 1191, 1110, 1062, 723 cm$^{-1}$.

$^1$H-NMR ($\delta$, CDCl$_3$): 0.88 (t, J=6.4 Hz), 1.10~1.85 (m, 76H), 1.85~2.10 (m, 4H), 2.29 (t, J=7.5 Hz, 2H), 2.39 (bt, J=7.6 Hz, 2H), 3.21~4.20 (m, 13H), 4.05 (t, J=6.7 Hz, 2H), 5.34 (bt, J=5.3 Hz, 2H).

EXAMPLE 11

Synthesis of
N-(2-hydroxy-3-hexadecyloxypropyl)-N-2-hydroxyethyl-16-(methylheptadecanoyloxy)hexadecanamide (II-Cc) [amide derivative of the above-mentioned general formula (II) wherein $R^3$ is $C_{16}H_{33}$— and $R^5O—R^4$ is

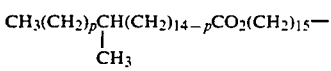

wherein is a group of integers having a distribution with a peat at p=7]

The procedure of Example 10 was repeated except that the oleoyl chloride employed in Example 10 (3) was replaced by methylheptadecanoyl chloride. Thus the target compound (II-Cc) was obtained (yield: 65.5 %). The melting point and IR and $^1$H-NMR data of the obtained compound are as follows:

m.p.: 60.1°~62.0° C.

IR: 3298, 2926, 2380, 1737, 1614, 1467, 1443, 1203, 1110, 1059, 720 cm$^{-1}$.

$^1$H-NMR (δ, CDCl$_3$): 0.77~1.00 (m, 9H), 1.03~1.75 (m, 81H), 2.29 (t, J=7.5 Hz, 2H), 2.40 (bt, J=7.3 Hz, 2H), 3.24~4.33 (m, 13H), 4.05 (t, J=6.6 Hz, 2H).

EXAMPLE 12

Synthesis of
N-(2-hydroxy-3-hexadecyloxypropyl)-N-2-hydroxyethyl-32-(9Z,12Z-octadecadienoyloxy)dotriacontanamide (II-Cd) [amide derivative of the above-mentioned general formula (II) wherein

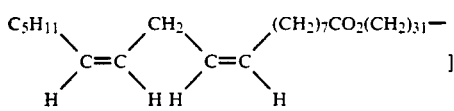

The procedure of Example 10 was repeated except that the methyl 16-hydroxyhexadecanoate employed in Example 10 (1) was replaced by methyl 32-hydroxydotriacontanoate and the oleoyl chloride employed in Example 10 (3) was replaced by linoleoyl chloride. Thus the target compound (II-Cd) was obtained (yield: 24.8 %). The melting point and IR and $^1$H-NMR data of the obtained compound are as follows:

m.p.: 72.4°~73.0° C.

IR: 3304, 2920, 2852, 1738, 1614, 1466, 1442, 1168, 1112, 1062, 760, 722 cm$^{-1}$.

$^1$H-NMR (δ, CDCl$_3$): 0.81~1.01 (m, 6H), 1.10~1.72 (m, 92H), 1.95~2.15 (m, 4H), 2.29 (t, J=7.5 Hz, 2H), 2.39 (bt, J=7.6 Hz, 2H), 2.77 (bt, J=5.7 Hz, 2H), 3.18~4.20 (m, 13H), 4.05 (t, J=6.7 Hz, 2H), 5.23~5.46 (m, 4H).

EXAMPLE 13

Synthesis of
N-(2-hydroxy-3-hexadecyloxypropyl)-N-2-hydroxyethyl-16-(12-hydroxyoctadecanoyloxy)hexadecanamide (II-Ce) [amide derivative of the above-mentioned general formula (II) wherein $R^3$ is $C_{16}H_{33}$— and $R^5O—R^4$ is

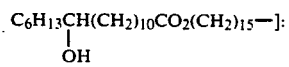

(1) Synthesis of
12-(tert-butyldimethylsilyloxy)octadecanoic acid 3.28 g (10 mmol) of ethyl 12-hydroxyoctadecanoate, 1.36 g (20 mmol) of imidazole and 50 ml of dimethylformamide were introduced into a 100-ml flask equipped with a stirrer and a dropping funnel. 1.66 g (11 mmol) of tert-butyldimethylchlorosilane was added dropwise thereto while stirring at room temperature. After the completion of the addition, the mixture was stirred at 50° C. for 18 hours to thereby complete the reaction. Next, the reaction mixture was extracted with ether and washed with brine. After removing the solvent under reduced pressure, the residue was purified by silica gel flash chromatography to thereby give ethyl 12-(tert-butyldimethylsilyloxy)octadecanoate.

Next, the ethyl 12-(tert-butyldimethylsilyloxy)octadecanoate thus obtained was introduced into a 100-ml flask equipped with a stirrer and 20 ml of ethanol and 2.24 g (20 mmol) of a 50% aqueous solution of KOH were added thereto. The obtained mixture was stirred at room temperature for 4 hours. After the completion of the reaction, the reaction mixture thus obtained was neutralized with hydrochloric acid and extracted with chloroform. After removing the solvent under reduced pressure, 4.0 g of 12-(tert-butyldimethylsilyloxy)octadecanoic acid was obtained (yield: 96.4 %).

(2) Synthesis of Amide Derivative (II-Ce)

1.87 g (4.5 mmol) of the 12-(tert-butyldimethylsilyloxy)actadecanoic acid obtained in the above step (1), 3.27 g (3 mmol) of the compound (XIII-b) obtained in Example 10 (2), 1.18 g (4.5 mmol) of triphenylphosphine and 10 ml of tetrahydrofuran were introduced into a 100-ml flask equipped with a stirrer, a dropping funnel and a thermometer. Then 0.71 g (4.05 mmol) of diethyl azodicarboxylate dissolved in 5 ml of tetrahydrofuran was added dropwise thereto in 5 minutes while stirring at room temperature. After the completion of the addition, the mixture was stirred for additional 4 hours at room temperature. After removing the solvent under reduced pressure, the residue was purified by silica gel flash column chromatography.

Then the intermediate thus obtained was introduced into a 100-ml flask equipped with a stirrer and 60 ml of tetrahydrofuran and 3.24 g (10.3 mmol) of tetrabutylammonium fluoride were added thereto. After heating to 60° C. and stirring for 24 hours, the obtained reaction mixture was extracted with chloroform and washed with brine. After removing the solvent under reduced pressure, the residue was purified by silica gel flash column chromatography. Thus 0.63 g of the title compound (II-Ce) was obtained (yield: 23.4 %). The melting point and IR and $^1$H-NMR data of the obtained compound are as follows:

m.p.: 71.7°~73.7° C.

IR: 3336, 2920, 2852, 1740, 1620, 1470, 1180, 1116, 1060, 722 cm$^{-1}$.

$^1$H-NMR (δ, CDCl$_3$): 0.89 (bt, J=6.2 Hz, 6H), 1.07~2.00 (m, 82H), 2.30 (t, J=7.5 Hz, 2H), 2.40 (bt, J=7.6 Hz, 2H), 3.22~4.21 (m, 15H), 4.06 (t, J=6.6 Hz, 2).

EXAMPLE 14

Synthesis of
N-(2-hydroxy-3-hexadecyloxypropyl)-N-2-hydroxyethyl-16-(9,10,12-trihydroxyoctadecanoyloxy)hexadecanamide (II-Cf) [amide derivative of the above-mentioned general formula (II) wherein R$^3$ is C$_{16}$H$_{33}$— and R$^5$O—R$^4$ is

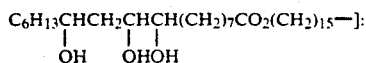

The procedure of Example 13 was repeated except that the ethyl 12-hydroxyoctadecanoate employed in Example 13 (1) was replaced by ethyl 9,10,12-trihydroxyoctadecanoate. Thus the target compound (II-Cf) was obtained (yield: 32.7%). The melting point and IR and $^1$H-NMR data of the obtained compound are as follows:

m.p.: 75.8°~79.2° C.

IR: 3300, 2924, 2856, 1728, 1620, 1470, 1178, 1120, 1070, 722 cm$^{-1}$.

$^1$H-NMR (δ, CDCl$_3$): 0.82~1.02 (m, 6H), 1.15~2.30 (m, 78H), 2.30 (t, J=7.4 Hz, 2H), 2.41 (bt, J=7.6 Hz, 2H), 3.22~4.26 (m, 19H), 4.07 (t, J=6.6 Hz, 2H).

EXAMPLE 15

Synthesis of
N-(2-hydroxy-3-hexadecyloxypropyl)-N-2-hydroxyethyl-12-(9Z,12Z-octadecadienoyloxy)dodecanamide (II-Cg) amide derivative of the above-mentioned general formula (II) wherein R$^3$ is C$_{16}$H$_{33}$— and R$^5$O—R$^4$ is

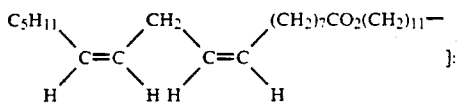

(1) Synthesis of
N-(2-hydroxy-3-hexadecyloxypropyl)-N-2-hydroxyethyl-12-(2-tetrahydropyranyloxy)dodecanamide (XI-g)

The procedure of Example 10 (1) was repeated except that the methyl 16-hydroxyhexadecanoate employed in Example 10 (1) was replaced by methyl 12-hydroxydodecanoate. Thus the target compound (XI-g) was obtained (yield: 67.8 %).

(2) Synthesis of
N-(2-acetoxy-3-hexadecyloxypropyl)-N-2-acetoxyethyl-12-hydroxydodecanamide (XIII-g)

167.0 g (0.23 mol) of the compound (XI-g) obtained in the above step (1), 91.0 g (1.15 mol) of pyridine and 440 ml of dichloromethane were introduced into a 1-l flask equipped with a stirred and a dropping funnel. Then 45.1 g (0.575 mol) of acetyl chloride was added dropwise thereto in 1.5 hours while stirring at 0° C. After the completion of the addition, the mixture was allowed to react for additional 1 hour to thereby complete the reaction. Next, 7.4 g (0.23 mol) of methanol was added to the reaction mixture to thereby react the excessive acetyl chloride. The mixture thus obtained was washed with water, 2 N hydrochloric acid and brine and then the solvent was removed under reduced pressure.

Then the intermediate thus obtained was introduced into a 1-l flask equipped with a stirrer and 368 g (0.115 mol) of methanol and 1.16 g (4.6 mmol) of pyridinium p-toluenesulfonate were added thereto. The obtained mixture was stirred at 40° C. for 5 hours. After the completion of the reaction, the mixture was neutralized by adding 0.76 g (9.2 mmol) of NaHCO$_3$. After removing the methanol, the residue was dissolved in chloroform and washed with brine. After removing the solvent under reduced pressure, the residue was purified by silica gel short column chromatography. Thus 118.3 g of the target compound (XIII-g) was obtained (yield: 80.1 %).

(3) Synthesis of Amide Derivative (II-Cg)

73.6 g (0.115 mol) of the compound (XIII-g) obtained in the above step (2), 160 ml of dichloromethane and 21.8 g (0.276 mol) of pyridine were introduced into a 1-l flask equipped with a stirrer and a dropping funnel. Then 41.2 g (0.138 mol) of linoleoyl chloride was added dropwise thereto in 30 minutes while stirring at 0° C. After the completion of the addition, the mixture was stirred for additional 2 hours. Next, 1.6 g (0.05 mol) of methanol was added thereto thereby convert the excessive linoleoyl chloride into methyl linoleate. Then the reaction mixture was washed with brine and the solvent was removed under reduced pressure. The residue was purified by silica gel short column chromatography.

Next, the intermediate thus obtained was introduced into a 3-l flask equipped with a stirrer. Then 1-l of ethanol, 0.5 l of methanol and 29.4 g (0.213 mol) of K$_2$CO$_3$ were added thereto and the obtained mixture was stirred at 0° to 10° C. for 1 hour. After the completion of the reaction, water was added to thereby dissolve the salt thus formed. Then the reaction mixture was extracted with diisopropyl ether and washed with brine. After removing the solvent under reduced pressure, the residue was purified by silica gel flash column chromatography to thereby give 62.0 g of the title compound (II-Cg) (yield: 65.7 %). The melting point and IR and $^1$H-NMR data of the obtained compound are as follows:

m.p.: 50.6°~52.8° C.

IR: 3304, 2924, 2856, 1734, 1616, 1470, 1176, 1108, 1060, 720 cm$^{-1}$.

$^1$-NMR (δ, CDCl$_3$): 0.82~0.95 (m, 6H), 1.13~1.74 (m, 62H), 1.96~2.13 (m, 4H), 2.29 (t, J=7.5 Hz, 2H), 2.39 (bt, J=7.6 Hz, 2H), 2.77 (bt, J=5.7 Hz, 2H), 3.22~4.21 (m, 13H), 4.05 (t, J=6.71 Hz, 2H), 5.23~5.48 (m, 4H).

EXAMPLE 16

Synthesis of N-(2-hydroxy-3-hexadecyloxypropyl)-N-2-hydroxyethyl-15-(9Z,12Z-octadecadienoyloxy)pentadecanamide (II-Ch) [amide derivative of the above-mentioned general formula (II) wherein $R^3$ is $C_{16}H_{33}-$ and $R^5O-R^4$ is

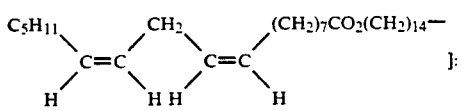 ]:

The procedure of Example 15 was repeated except that the methyl 12-hydroxydodecanoate employed in Example 15 (1) was replaced by methyl 15-hydroxypentadecanoate. Thus the target compound (II-Ch) was obtained (yield: 42.3 %). The melting point and IR and $^1$H-NMR data of the obtained compound are as follows:

m.p.: 64.2°~65.7° C.

IR: 3312, 2924, 2856, 1734, 1618, 1466, 1440, 1186, 1110, 1060, 722 cm$^{-1}$.

$^1$-NMR (δ, CDCl$_3$): 0.82~0.97 (m, 6H), 1.15~1.63 (m, 58H), 1.96~2.14 (m, 4H), 2.29 (t, J=7.5 Hz, 2H), 2.39 (bt, J=7.6 Hz, 2H), 2.77 (bt, J=5.7 Hz, 2H), 3.21~4.20 (m, 13H), 4.05 (t, J=6.7 Hz, 2H), 5.23~5.48 (m, 4H).

EXAMPLE 17

The dermatologic preparations of the present invention comprising 10% of each of the amide derivatives of the present invention listed in Table 4 and 90% of squalane were prepared. Then the transepidermal water loss and percutaneous absorption of each of the dermatologic preparations were evaluated in the same manner as those described in Example 4. For comparison, a comparative dermatologic preparation comprising squalane alone was also evaluated. Table 4 summarizes the results.

TABLE 4

| Amide derivative | Transepidermal water loss | Percutaneous absorption |
| --- | --- | --- |
| Invention product | | |
| compound of Ex. 6 (II-Aa) | 26.7 ± 7.3 | 779 ± 76.6 |
| compound of Ex. 7 (II-Ab) | 28.0 ± 8.4 | 516 ± 172 |
| compound of Ex. 8 (II-Ba) | 12.4 ± 3.2 | 340 ± 122 |
| compound of Ex. 9 (II-Ca) | 14.2 ± 4.2 | 124 ± 36.2 |
| compound of Ex. 10 (II-Cb) | 18.2 ± 6.3 | 242 ± 27 |
| compound of Ex. 11 (II-Cc) | 18.8 ± 7.4 | 200 ± 15 |
| compound of Ex. 12 (II-Cd) | 12.5 ± 3.8 | 33.6 ± 3.0 |
| compound of Ex. 13 (II-Ce) | 16.2 ± 9.1 | 464 ± 12 |
| compound of Ex. 14 (II-Cf) | 12.3 ± 3.4 | 626 ± 69 |
| compound of Ex. 15 (II-Cg) | 11.4 ± 5.8 | 112 ± 25 |
| compound of Ex. 16 (II-Ch) | 15.8 ± 6.3 | 210 ± 47 |
| Comparative product | | |
| squalane alone | 35.8 ± 9.6 | 1220 ± 240 |

EXAMPLE 18

By using each of the amide derivatives of the present invention, the dermatologic preparations of the present invention of the composition as specified in Table 5 (emulsion cosmetic) were prepared. The effect of each product of improving skin chapping was evaluated in the same manner as the one described in Example 5. For comparison, a dermatologic preparation free from any amide derivative of the present invention (comparative product) was evaluated in the same manner. Table 5 summarizes the results.

TABLE 5

| | Invention products | (% by weight) Comparative product |
| --- | --- | --- |
| methyl-branched isostearyl glyceryl ether | 2.0 | 2.0 |
| 2-octyldodecyl myristate | 10.0 | 10.0 |
| vaseline | 3.0 | 3.0 |
| squalane | 5.0 | 5.0 |
| tocopherol acetate | 0.5 | 0.5 |
| amide derivative (refer to Table 6) | 1.0 | — |
| water | the balance | the balance |

TABLE 6

| Amide derivative | Transepidermal water loss | Skin chapping score |
| --- | --- | --- |
| Invention product | | |
| compound of Ex. 6 (II-Aa) | 25.4 ± 7.8 | 1.3 ± 0.3 |
| compound of Ex. 7 (II-Ab) | 22.8 ± 6.8 | 1.2 ± 0.4 |
| compound of Ex. 8 (II-Ba) | 12.1 ± 4.2 | 0.8 ± 0.3 |
| compound of Ex. 9 (II-Ca) | 12.3 ± 4.3 | 0.9 ± 0.3 |
| compound of Ex. 10 (II-Cb) | 16.4 ± 4.8 | 1.62 ± 0.3 |
| compound of Ex. 11 (II-Cc) | 16.6 ± 5.3 | 1.7 ± 0.3 |
| compound of Ex. 12 (II-Cd) | 11.6 ± 3.3 | 0.9 ± 0.2 |
| compound of Ex. 13 (II-Ce) | 14.6 ± 7.2 | 1.6 ± 0.6 |
| compound of Ex. 14 (II-Cf) | 11.3 ± 3.3 | 1.2 ± 0.5 |
| compound of Ex. 15 (II-Cg) | 10.6 ± 5.2 | 1.0 ± 0.4 |
| compound of Ex. 16 (II-Ch) | 14.8 ± 5.7 | 1.6 ± 0.8 |
| Comparative Product | | |
| — | 28.6 ± 9.8 | 2.4 ± 0.7 |

What is claimed is:

1. N-(2-hydroxy-3-hexadecyloxypropyl)-N-2-hydroxyethyl-16-(9Z-octadecenoyloxy)hexadecanamide, N-2-hydroxy-3-hexadecyloxypropyl)-N-16-(methylheptadecanoyloxy) hexadecanamide, N-(2-hydroxy-3-hexadecyloxypropyl)-N-2-hydroxyethyl-32-(9Z,12Z-octadecadienoyloxy)-dotriacontanamide, N-(2-hydroxy-3-hexadecyloxypropyl)-N-2-hydroxyethyl-16-(12-hydroxyoctadecanoyloxy)hexadecanamide, N-(2-hydroxy-3-hexadecyloxypropyl)-N-2-hydroxyethyl-16-(9,10,12-trihydroxyoctadecanoyloxy)hexadecanamide, N-(2-hydroxy-3-hexadecyloxypropyl)-N-2-hydroxyethyl-12-(9Z,12Z-octadecadienoyloxy)-dodecanamide, and N-(2-hydroxy-3-hexadecyloxypropyl)-N-2-hydroxyethyl-15-(9Z,12Z-octadecadienoyloxy)-pentadecanamide.

2. A dermatologic preparation comprising as an active ingredient an effective amount of an amide derivative as claimed in claim 1, together with a suitable dermatologic base.

* * * * *